United States Patent
Al Mourabit et al.

(10) Patent No.: US 7,838,681 B2
(45) Date of Patent: Nov. 23, 2010

(54) SYNTHESIS OF SUBSTITUTED HETEROCYCLIC COMPOUNDS

(75) Inventors: Ali Al Mourabit, Gif-suf-Yvette (FR); Nathalie Travert, Gif-sur-Yvette (FR); Robert Abou-Jneid, Paris (FR); Saïd Ghoulami, Orsay (FR)

(73) Assignees: Centre National de la Recherche Scientifique (C.N.R.S.), Paris (FR); Universite de Paris Sud, Orsay (FR)

( * ) Notice: Subject to any disclaimer, the term of this patent is extended or adjusted under 35 U.S.C. 154(b) by 986 days.

(21) Appl. No.: 10/555,740

(22) PCT Filed: Apr. 30, 2004
(Under 37 CFR 1.47)

(86) PCT No.: PCT/FR2004/001059
§ 371 (c)(1),
(2), (4) Date: Nov. 29, 2006

(87) PCT Pub. No.: WO2004/101573
PCT Pub. Date: Nov. 25, 2004

(65) Prior Publication Data
US 2007/0106077 A1    May 10, 2007

(30) Foreign Application Priority Data
May 7, 2003    (FR) .................................. 03 05569

(51) Int. Cl.
C07D 403/12    (2006.01)
C07D 233/88    (2006.01)
C07D 263/48    (2006.01)
C07D 277/40    (2006.01)

(52) U.S. Cl. ........................ 548/194; 548/195; 548/233; 548/314.7; 548/331.5; 548/332.5

(58) Field of Classification Search ................ 548/194, 548/195, 233, 314.7, 331.5, 332.5
See application file for complete search history.

(56) References Cited

U.S. PATENT DOCUMENTS
6,441,013 B1    8/2002   Greiner et al.

OTHER PUBLICATIONS

International Search Report for PCT/FR2004/001059 dated 8 Nov. 2004.

*Primary Examiner*—Patricia L Morris
(74) *Attorney, Agent, or Firm*—Nixon & Vanderhye P.C.

(57) ABSTRACT

The invention relates to a method of synthesizing heterocyclic compounds. The invention is characterised in that it consists in opening a compound having formula (I), wherein: —X represents NH, O, S or a N-p group, p being a protective group, such as Boc or Troc; —Y represents N, O, S; —Z represents $NH_2$ or NH-p; and —$R_1$ represents a $C_1$-$C_6$ alkoxy radical, aryloxy, such as phenyloxy, or a pyrrolyl radical, said radicals being optionally substituted, or the salts thereof, and the isomers of the aforementioned compounds. Moreover, the above-mentioned opening step is performed in conditions such as to produce a heterocycle having formula (II), wherein: —X, Y and Z are as defined above; —$R_2$ represents a —CH=CH—$CH_2$—NH—$COR_1$ or —CH=CH—$CH_2$—NH—CO group; and $R_3$ occupies one, two or three positions and represents a halogen. The invention can be used to synthesise natural products.

20 Claims, No Drawings

SYNTHESIS OF SUBSTITUTED HETEROCYCLIC COMPOUNDS

This application is the US national phase of international application PCT/FR2004/001059 filed 30 Apr. 2004, which designated the U.S. and claims priority to FR 03/05569 filed 7 May 2003, the entire contents of each of which are hereby incorporated by reference.

The invention relates to the synthesis of substituted heterocyclic compounds. It is targeted more especially at a process of the synthesis of 5-membered heterocycles of structure H:

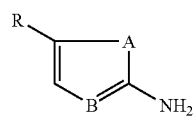

(H)

in which A and B are heteroatoms, it being possible for A to be substituted depending on the nature of the heteroatom, and R is a substituent group.

It is known that such compounds can be used for the synthesis of precursors of numerous natural products having properties of great interest, in particular in the pharmaceutical field, especially for the synthesis of alkaloids of marine origin, of azasugar derivatives and of analogs of these products.

Numerous studies have thus been directed at the search for routes which make possible the synthesis of such products. However, the processes provided to date are complex and thus expensive and have yields which are not very satisfactory.

The inventors have found that these problems could be overcome by opening biheterocycles of structure B—H:

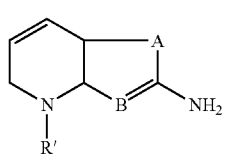

(B-H)

in which A and B are as defined above and R' is a substituent group.

An object of the invention is thus to provide a process for the production of 5-membered heterocycles comprising two heteroatoms which are substituted.

It is also targeted at the production of these bicycles from dihydropyridines.

In addition, the invention relates to the novel heterocycles obtained and to the intermediate bicycles.

It furthermore relates to the applications of this process and of the products obtained in the synthesis of natural products or analogs of such products.

The process for the synthesis of heterocyclic compounds of the invention is characterized in that it comprises the opening of a compound of formula I:

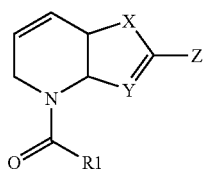

(I)

in which,

X represents NH, O, S or an N-p group, p being a protective group, such as Boc or Troc, Y represents N, O or S, Z represents $NH_2$ or NH-p, and $R_1$ represents a $C_1$-$C_6$ alkoxy radical, an aryloxy radical, in particular a phenyloxy radical, or a pyrrolyl radical, these radicals optionally being substituted, or of their salts, and of the isomers of these compounds, said stage of opening being carried out under conditions resulting in a heterocycle of formula II:

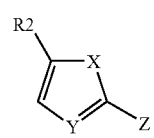

(II)

in which,

X, Y and Z are as defined above, and $R_2$ represents a —CH=CH—$CH_2$—NH—$COR_1$ or

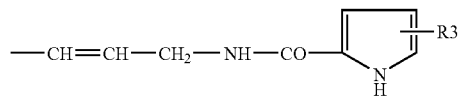

group, $R_3$ occupying one, two or three positions and representing a halogen.

The stage of opening the bicycle is advantageously carried out in an alkaline medium or a solvent, such as DMSO, by heating at reflux.

In an alternative form, in particular when $R_1$ represents a pyrrolyl group, if appropriate substituted, the bicycle is reacted, in solution in a solvent, such as dichloromethane, with trifluoroacetic acid at ambient temperature.

The stage of opening is carried out in particular on a mixture of regioisomers of formula I.

Preferably, use is made of a salt of a compound of formula I.

In a preferred embodiment of the invention, the compounds of formula I are hydroimidazopyridines, X and Y comprising N as heteroatoms.

They are hydroimidazopyridines of formula III:

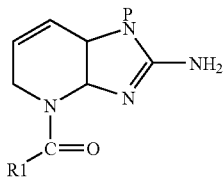
(III)

or of formula IV:

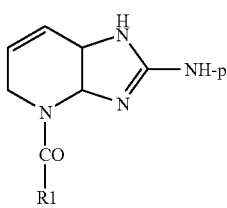
(IV)

Advantageously, the stage of opening according to the invention is carried out on a salt of these hydroimidazopyridines. This salt exhibits the formula V or VI:

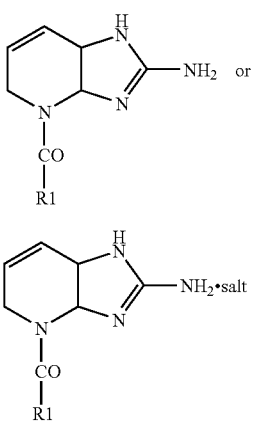
(V)

(VI)

Mention will be made, among the appropriate salts, purely by way of illustration, of hydrochlorides, acetates and trifluoroacetates.

In another preferred embodiment of the invention, the compounds of formula I subjected to the stage of opening are hydrooxazopyridines, X representing the heteroatom O.

Preferred compounds correspond to the formula VII:

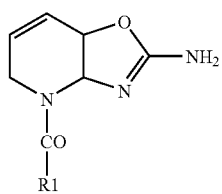
(VII)

On bringing to reflux a solution of these compounds in a solvent, such as DMF, bicycles of formula VIII are obtained.

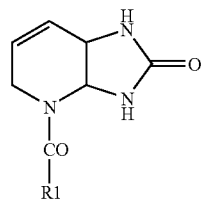
(VIII)

In yet another preferred embodiment of the invention, the compounds of formula I are hydrothiazopyridines, X representing the heteroatom S.

The compounds of formula II obtained by opening the compounds of formula I defined above are substituted by a free allylamine chain or an allylamine chain protected in the carbamate form, $—CH=CH—CH_2—NH_2R_1$, allylamide $—CH=CH—CH_2—NH—COR_1$ or

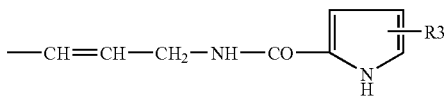

$R_3$ occupying one, two or three positions and representing a halogen.

According to another additional provision of the invention, when it is desired to obtain the compounds of formula II in the form of salts, they are reacted with an appropriate acid as mentioned above.

The bicycles of formula I are advantageously obtained by reaction of a dihydropyridine of formula IX:

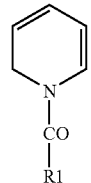
(IX)

with a derivative of formula X:

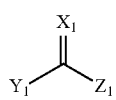
(X)

in which:
$X_1$ represents O, S or NH, and
$Y_1$ and $Z_1$ represent $NH_2$.

This reaction between the compounds of formulae IX and X is advantageously carried out in the presence of bromine in organic solvents, such as DMF and/or $CH_3CN$, at ambient temperature and under argon.

The products obtained are recovered and purified, if desired, for example by chromatography, and the isomers are separated, if desired.

The invention is also targeted, as novel products, at the compounds of formula II and, as intermediates, at the compounds of formula I as defined above.

The compounds of the invention can advantageously be used for the rapid synthesis of natural precursors, for example of alkaloids of marine origin, such as hymenidin, chlathrodin and oroidin, for the synthesis of products analogous to alkaloids of marine origin, such as girolline, or for the synthesis of azasugar derivatives, if appropriate substituted and functionalized.

The invention thus provides the means for obtaining, by the synthetic route, biogenetic precursors of products having therapeutic properties of great interest, in particular exhibiting immunosuppressant, antitumor, antimicrobial and antiviral activities or also an anticraving activity.

Other characteristics and advantages of the invention are given in the examples which follow:

EXAMPLE 1

(cis)-2-Amino-5,7a-dihydro-3aH-imidazo[4,5-b]pyridine-1,4-dicarboxylic acid 1-tert-butyl ester 4-methyl ester (2) and (cis)-2-tert-butoxycarbonylamino-1,3a,5,7a-hexahydroimidazo[4,5-b]pyridine-4-carboxylic acid methyl ester (3)

intermediates, the compounds of formula I as defined above.

The compounds of the invention can advantageously be used for the rapid synthesis of natural precursors, for example of alkaloids of marine origin, such as hymenidin, chlathrodin and oroidin, for the synthesis of products analogous to alkaloids of marine origin, such as girolline, or for the synthesis of azasugar derivatives, if appropriate substituted and functionalized.

The invention thus provides the means for obtaining, by the synthetic route, biogenetic precursors of products having therapeutic properties of great interest, in particular exhibiting immunosuppressant, antitumor, antimicrobial and antiviral activities or also an anticraving activity.

Other characteristics and advantages of the invention are given in the examples which follow:

EXAMPLE 1

(cis)-2-Amino-5,7-dihydro-3aH-imidazo[4,5-b]pyridine-1,4-dicarboxylic acid 1-tert-butyl ester 4-methyl ester (2) and (cis)-2-tert-butoxycarbonylamino-1,3a,5,7-hexahydroimidazo[4,5-b]pyridine-4-carboxylic acid methyl ester (3)

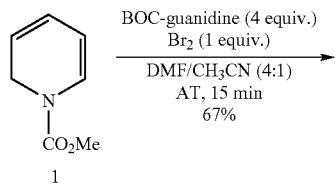

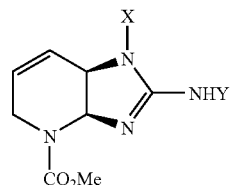

2: X = Boc, Y = H
3: X = H, Y = Boc

A solution of Br$_2$ (0.49 ml, 9.57 mmol, 1 equiv.) in DMF (5 ml) is added over 15 min to a solution of N-methoxycarbonyl-1,2-dihydropyridine 1 (1.33 g, 9.57 mmol, 1 equiv.) and of Boc-guanidine (6.1 g, 38.3 mmol, 4 equiv.) in a mixture of DMF (15 ml) and of CH$_3$CN (5 ml) at ambient temperature and under argon. The reaction being complete from the end of the addition of the bromine, the solvent is evaporated at 50° C. and the crude product (11 g) is chromatographed on silica gel using dichloromethane saturated with ammonia. The regioisomers 2 and 3 are obtained as a mixture, in the form of a hygroscopic yellow solid (1.9 g, 67%). The two products can be easily separated by chromatography on a thick silica layer and analyzed separately:

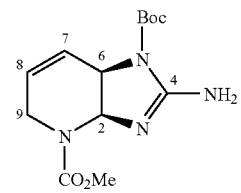

Regioisomer 2: yellow solid; M.p.=75.5° C. (dec.); $^1$H NMR (300 MHz, CD$_3$OD): δ=1.55 (s, 9H, (CH$_3$)$_3$), 3.63 (m, 4H, 9-H$_a$), 3.75 (s, 6H, OCH$_3$), 4.19 (dd, J=18 and 2 Hz, 1H, 9-H$_b$), 4.63 (m, 1H, 6-H), 5.82 (m, J=2 and 11 Hz, 1H, 7-H), 6.07 (broad m, 2H, 2-H and 8-H); $^{13}$C NMR (75.5 MHz, CD$_3$OD): δ=28.3 (CH$_3$)$_3$, 39.6 (C-9), 53.5 (C-3'), 55.0 (C-6), 70.0 (C-2), 84.4 (C-8''), 122.0 (C-7), 129.0 (C-8), 153.0, 156.0, 158.0 (C-4, CO carbamate); MS(ES): m/z 296.9 [M+H]$^+$, 196.8 [M+H−Boc]$^+$; HRMS, calculated C$_{13}$H$_{20}$O$_4$N$_4$ [M+H]$^+$: 297.15628, found: 297.15605.

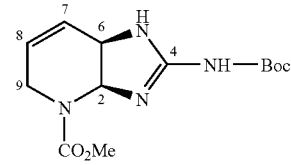

Regioisomer 3: yellow solid; M.p.=117° C. (dec.); $^1$H NMR (300 MHz, CD$_3$OD): =1.47 (s, 9H, (CH$_3$)$_3$), 3.47 (d, 18 Hz, 1H, 9-H$_a$), 3.75 (s, 3H, OCH$_3$), 4.12 (broad d, J=8 Hz, 1H, 6-H), 4.31 (broad d, J=18 Hz, 2H, 9-H$_b$), 5.62 (dd, J=2 and 11 Hz, 1H, 7-H), 5.85 (broad s, 1H, 8-H), 6.46 (broad s, 1H, 2-H); $^{13}$C NMR (75.5 MHz, CD$_3$OD): δ=28.4 (CCH$_3$), 39.1 (C-9), 53.6 (OCH$_3$), 55.9 (C-6), 70.2 (C-2), 84.8 C(tBu), 124.3 (C-8), 127.5 (C-7); MS(ES): m/z 296.9 [M+H]$^+$, 196.8 [M+H−Boc]$^+$; HRMS, calculated C$_{13}$H$_{20}$O$_4$N$_4$ [M+H]$^+$: 297.15628, found: 297.15769.

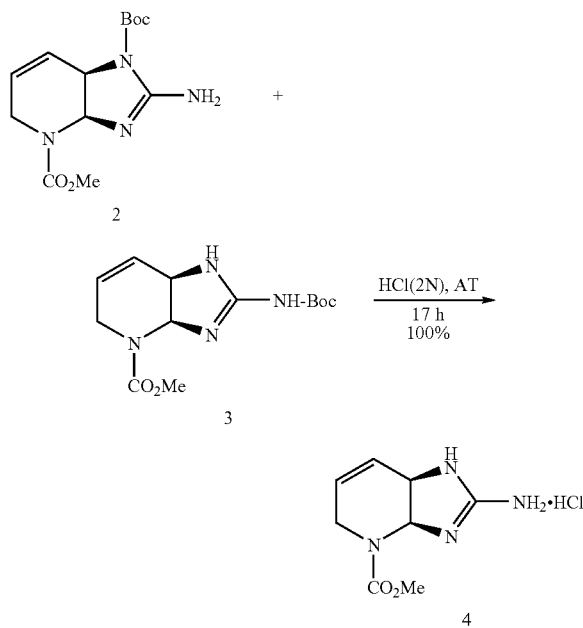

EXAMPLE 2

(cis)-2-Amino-1,3a,5,7a-tetrahydroimidazo[4,5-b]pyridine-4-carboxylic acid methyl ester hydrochloride 4

A solution of the mixture of products 2 and 3 (124 mg, 0.42 mmol) in 2M HCl (9 ml) is left stirring for 17 h at ambient temperature and is then concentrated to dryness. The product 4 is obtained in the form of the brown semisolid hydrochloride (99 mg, 0.42 mmol, quantitative).

EXAMPLE 3

Synthesis of the Deprotected Product 4 from the Dihydropyridine and Without Purification of the Regioisomers

A solution of $Br_2$ (0.73 ml, 14.3 mmol, 1 equiv.) in DMF (5 ml) is added over 15 min to a solution of N-methoxycarbonyl-1,2-dihydropyridine 1 (2 g, 14.3 mmol, 1 equiv.) and of Boc-guanidine (9.15 g, 57.5 mmol, 4 equiv.) in a mixture of DMF (10 ml) and of $CH_3CN$ (5 ml) under cold conditions (0-5° C.) and under argon. The reaction being complete from the end of the addition of bromine, the reaction mixture is poured onto ice-cold water (600 ml). The aqueous phase is subsequently extracted with DCM (3×200 ml). The crude product obtained (3.5 g) is dissolved in the minimum amount of methanol, followed by addition of a 2N hydrochloric acid solution (10 ml). The solution is brought to reflux in [illegible] for 5 min. After cooling, the reaction mixture is washed with ether and then evaporated to dryness to give 2.4 g of the deprotected compound 4 with a yield of 71% over the two stages.

$^1$H NMR (300 MHz, $CD_3OD$): δ=3.69 (broad d, J=19 Hz, 1H, 9-$H_b$), 3.79 (s, 3H, $OCH_3$), 4.25 (broad dd, J=19 and 4 Hz, 1H, 9-$H_a$), 4.47 (broad d, J=9 Hz, 1H, 6-H), 5.74 (qd, J=10 Hz, 1H, 7-H), 6.08 (broad dd, J=10 and 4 Hz, 1H, 8-H), 6.39 (d, J=8 Hz, 1H, 2-H); $^{13}$C NMR (75.5 MHz, $CD_3OD$): δ=39.7 (C-9), 52.0 (C-6), 54.0 ($OCH_3$), 66.0 (C-2), 123.0 (C-7), 128.0 (C-8), 157.0, 160.0 (CO carbamate, C-4); MS(ES): m/z 196.8 [M+H]$^+$; HRMS, calculated $C_8H_{12}O_2N_4$ [M+H]$^+$: 197.10385, found: 197.10314.

EXAMPLE 4

(cis)-2-Amino-5,7a-dihydro-3aH-oxazolo[4,5-b]pyridine-4-carboxylic acid methyl ester 5

A solution of $Br_2$ (1 ml, 19.3 mmol, 1 equiv.) in DMF (5 ml) is added over 20 min to a solution of N-methoxycarbonyl-1,2-dihydropyridine 1 (2.68 g, 19.3 mmol, 1 equiv.) and of urea (2.3 g, 38.6 mmol, 3 equiv.) in a mixture of DMF (19 ml) and of $CH_3CN$ (6 ml) at ambient temperature and under argon. The reaction being complete from the end of the addition of the bromine, the reaction mixture is concentrated to dryness. The residue is dissolved in methanol (30 ml), poured onto ice-cold water (150 ml) and then filtered through a Buchner funnel. The filtrate is basified (5% $Na_2CO_3$) until a pH of greater than 10 is obtained. After extracting with dichloromethane (4×100 ml), the aqueous phase is saturated with NaCl and then reextracted with dichloromethane (4×100 ml). After drying over $MgSO_4$ and evaporating the solvent, the solid obtained (5.94 g) is chromatographed on silica gel using dichloromethane (DCM) saturated with ammonia and then DCM saturated with $NH_3$:MeOH, 98:2. The product is obtained in the form of a beige solid (1.9 g, 50%).

EXAMPLE 5

(cis)-2-Amino-5,7a-dihydro-3aH-thiazolo[4,5-b]pyridine-4-carboxylic acid methyl ester 6

A solution of $Br_2$ (0.71 ml, 13.9 mmol, 1 equiv.) in DMF (5 ml) is added over 10 min to a solution of N-methoxycarbonyl-1,2-dihydropyridine 1 (1.92 g, 13 mmol, 1 equiv.) and of thiourea (3.95 g, 52 mmol, 4 equiv.) in DMF (15 ml)/$CH_3CN$ (5 ml) at ambient temperature and under argon. The reaction being complete from the end of the addition of the bromine, the reaction mixture is concentrated approximately twofold, poured onto ice-cold water (200 ml) and then filtered through a Buchner funnel. The filtrate is basified (5% $Na_2CO_3$) until a pH of greater than 10 is obtained and is then saturated with NaCl. After extracting with DCM, drying over $MgSO_4$ and evaporating the solvent, the liquid obtained (10.8 g) is chromatographed on silica gel using DCM (sat. $NH_3$) and then DCM (sat. $NH_3$)/MeOH, 2%. The product 6 ($R_f$=0.39, DCM/MeOH($NH_3$), 98:2) is obtained in the form of a white solid (0.32 g, 11%).

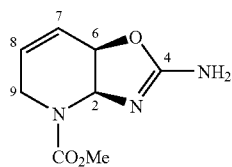

5

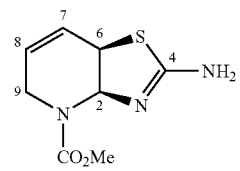

6

Beige solid, M.p.=1760 (dec.); $^1H$ NMR (300 MHz, $CD_3OD$): δ=3.65 (broad d, J=18 Hz, 1H, 9-$H_a$), 3.75 (s, 3H, 3'-H), 4.18 (dd, J=18 and 4 Hz, 1H, 9-$H_b$), 5.0 (dd, J=8 and 4 Hz, 1H, 6-H), 5.7 (m, J=4 and 11 Hz, 1H, 7-H), 6.1 (dd, J=11 and 4 Hz, 1H, 8-H), 6.27 (broad d, J=8 Hz, 1H, 2-H); $^1H$ NMR (300 MHz, $d_6$-DMSO): δ=3.50 (broad d, J=18 Hz, 1H, 9-$H_a$), 3.63 (s, 3H, $OCH_3$), 4.04 (broad dd, J=18 and 4 Hz, 1H, 9-$H_b$), 4.91 (dd, J=8 and 4 Hz, 1H, 6-H), 5.65 (broad d, J=11 Hz, 1H, 7-H), 6.1 (m, 4H, 2-H, 8-H, $NH_2$); $^{13}C$ NMR (75.5 MHz, $d_6$-DMSO): =38.3 (C-9), 52.5 ($OCH_3$), 70.7 (C-6), 72.6 (C-2), 122.3 (C-7), 129.0 (C-8), 155.4 (CO carbamate), 160.6 (C-4); MS(ES): m/z 197.9 $[M+H]^+$; HRMS, calculated for $C_8H_{11}O_3N_3$ $[M+H]^+$: 198.08787, found: 198.08771; Elem. Anal. for $C_8H_{11}O_3N_3$: calculated C(48.73%), H(5.58%), N(21.32%), O(24.37%); found C(48.49%), H(5.67%), N(21.32%), O(24.27%).

$^1H$ NMR (300 MHz, $d_6$-acetone): δ=3.64 (broad m, 9-$H_a$), 3.70 (s, 3H, $OCH_3$), 4.17 (d, J=17 Hz, 1H, 9-$H_b$), 4.30 (m, 6-H), 5.50 (m, J=2 Hz, J=10 Hz, 1H, 7-H); 5.76 (m, 1H, 8-H), 6.19 (m, 1H, 2-H). $^{13}C$ NMR (75.5 MHz, $d_6$-DMSO): δ=38.6 (C-9), 47.5 (C-6), 52.6 ($OCH_3$), 79.0 (C-2), 123.5 (C-7), 125.7 (C-8), 155.2 (C-4), 156.9 (CO carbamate). MS(EI): m/z=213$[M]^+$.

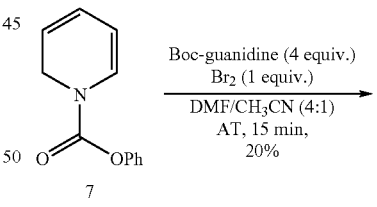

7

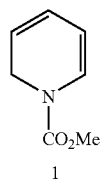

1 thiourea (4 equiv.)
$Br_2$ (1 equiv.)
⎯⎯⎯⎯⎯⎯⎯⎯→
DMF/$CH_3CN$ (4:1)
AT, 10 min, 11%

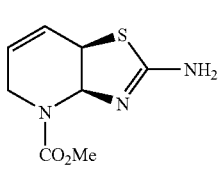

6

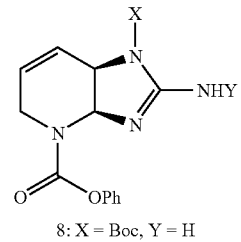

8: X = Boc, Y = H
9: X = H, Y = Boc

EXAMPLE 6

(cis)-2-Amino-5,7a-dihydro-3aH-imidazo[4,5-b]pyridine-1,4-dicarboxylic acid 1-tert-butyl ester 4-phenyl ester 8 and (cis)-2-tert-butoxycarbonylamino-1,3a,5,7a-hexahydroimidazo[4,5-b]pyridine-4-carboxylic acid phenyl ester 9

A solution of $Br_2$ (0.36 ml, 7 mmol, 1 equiv.) in DMF (5 ml) is added over a period of 15 min to a solution of N-phenyloxycarbonyl-1,2-dihydropyridine 7 (1.42 g, 7 mmol, 1 equiv.) and of Boc-guanidine (4.5 g, 28 mmol, 4 equiv.) in DMF (15 ml)/$CH_3CN$ (5 ml) at ambient temperature and under argon. The reaction being complete from the end of the addition of the bromine, the solvent is evaporated under vacuum and the crude product (2 g) chromatographed on silica gel (DCM sat. $NH_3$). The two regioisomers ($R_f$=0.40, DCM($NH_3$)) are obtained in the form of a white solid (1.9 g, 6.42 mmol, 20%). The two products 8 and 9 are easily purified by thick layer chromatography.

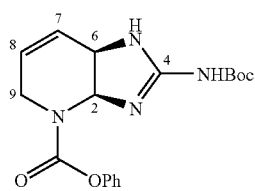

8

(cis)-2-Amino-5,7a-dihydro-3aH-imidazo[4,5-b]pyridine-1,4-dicarboxylic acid 1-tert-butyl ester 4-phenyl ester 8

$^1$H NMR (300 MHz, $CD_3OD$): δ=1.56 (s, 9H, $(CH_3)_3$), 3.78 (dd, 1H, 9-$H_a$, J=18 Hz), 4.33 (dd, J=18 Hz, 1H, 9-$H_b$), 4.73 (m, 1H, 6-H), 5.88 (broad d, 1H, J=10 Hz, 7-H), 6.11 (m, 1H, 8-H), 6.24 (dd, J=8 Hz, 1H, 2-H), 7.26 (m, 5H, H-phenyl); $^{13}$C NMR (75.5 MHz, $CD_3OD$): δ 28.7 (C($CH_3)_3$), 40.1 (C-9), 55.6 (C-6), 70.5 (C-2), 84.8 (CtBu), 122.8 (C-8), 127.1 (C-7), 123.3, 130.7 (C-Ph), 153.0 (C-4); MS(EI): m/z 358 $[M]^+$, 257 $[M-Boc]^+$.

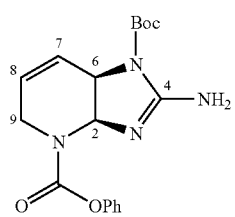

9

(cis)-2-tert-Butoxycarbonylamino-1,3a,5,7a-tetrahydro-imidazo[4,5-b]pyridine-4-carboxylic acid phenyl ester 9

$^1$H NMR (300 MHz, $CD_3OD$): δ=1.46 (s, 9H, $(CH_3)_3$), 3.57 (dd, J=19 Hz, 1H, 9-$H_a$), 4.18 (d, J=8 Hz, 1H, 6-H), 4.40 (dd, J=19 Hz, H, 9-$H_b$), 5.68 (m, 1H, 7-H), 5.87 (m, 1H, 8-H), 6.55 (dd, J=8 Hz, 1H, 2-H), 7.22 (m, 5H, H-phenyl); $^{13}$C NMR (75.5 MHz, $CD_3OD$): δ=28.9 (($CH_3)_3$), 40.1 (C-9), 56.5 (C-6), 70.5 (C-2), 85.8 (CtBu), 122.8 (C-Ph), 124.8 (C-8), 127.1 (C-7), 128.3, 130.7 (C-Ph); MS(EI): m/z 358 $[M]^+$, 257 $[M-Boc]^+$.

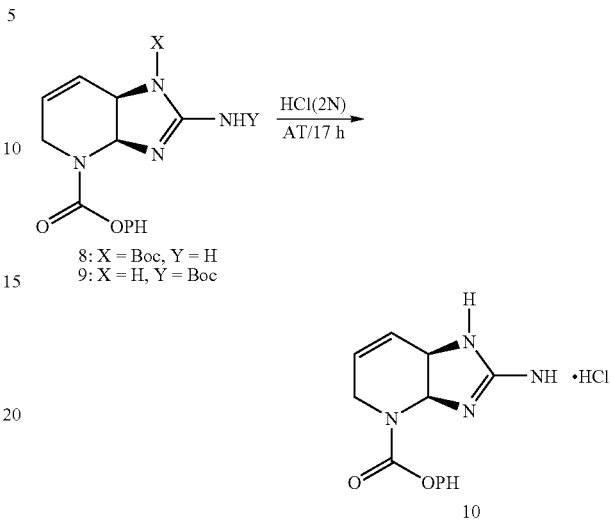

8: X = Boc, Y = H
9: X = H, Y = Boc

EXAMPLE 7

(cis)-2-Amino-1,3a,5,7a-tetrahydro-imidazo[4,5-b]pyridine-4-carboxylic acid phenyl ester hydrochloride 10

A solution of a mixture of products 8 and 9 (54 mg, 0.15 mmol) in HCl (2M, 5 ml) is stirred at ambient temperature for 17 h and then concentrated to dryness. The product 10 ($R_f$=0.5, acetone/AcOEt/water/HCOOH, 30:50:5:5) is obtained in the form of a brown-yellow solid (37 mg, 84%).

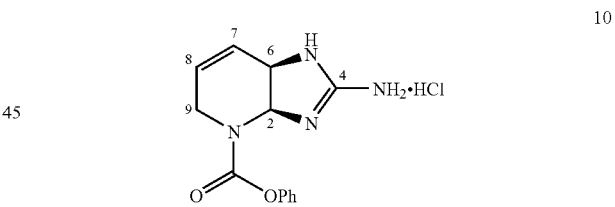

10

$^1$H NMR (300 MHz, $CD_3OD$): δ=3.84 (dd, J=18 Hz, 1H, 9-$H_a$), 4.36 (dd, J=18 Hz, H, 9-$H_b$), 4.53 (broad s, 1H, 6-H), 5.78 (dd, 1H, and 5 Hz, 7-H=10), 6.13 (broad m, 1H, 8-H), 6.50 (broad m, 1H, 2-H), 7.32 (m, 5H, H-phenyl); $^{13}$C NMR (75.5 MHz, $CD_3OD$): δ=40.2 (C-9), 52.1 (C-6), 66.6 (C-2), 123.2 (C-8), 127.4 (C-7), 130.8, 130.9 (C-Ph), 152.7 (C-4), 160.5 (carbamate); MS(ES): m/z 259.2 $[M+H]^+$.

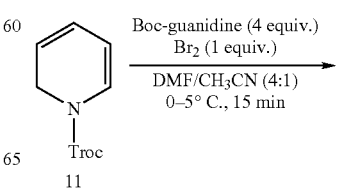

11

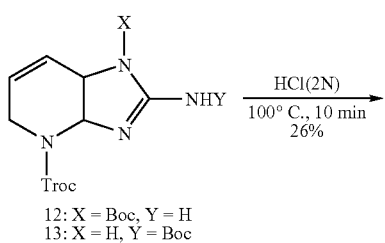

12: X = Boc, Y = H
13: X = H, Y = Boc

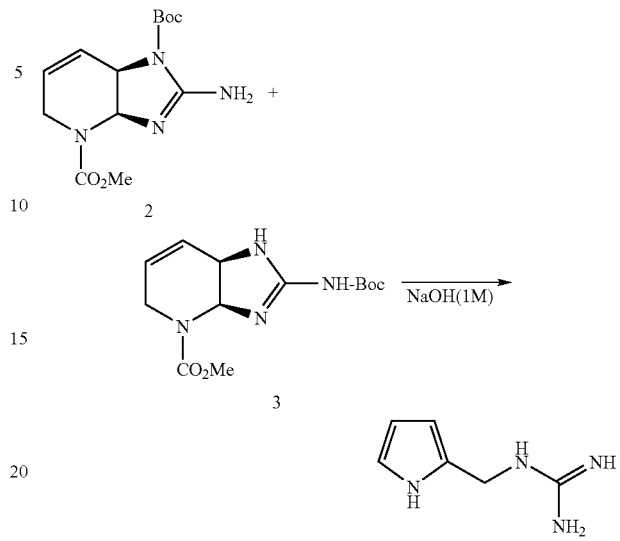

EXAMPLE 8

(cis)-2-Amino-1,3a,5,7a-tetrahydro-imidazo[4,5-b]pyridine-4-carboxylic acid 2,2,2-trichloroethyl ester hydrochloride A solution of Br$_2$ (0.79 ml, 15.5 mmol, 1 equiv.) in DMF (5 ml) is added over a period of 15 min to a solution of N-trichloroethylcarbonyl-1,2-dihydropyridine 11 (4 g, 15.5 mmol, 1 equiv.) and of Boc-guanidine (10 g, 62.0 mmol, 4 equiv.) in DMF (10 ml)/CH$_3$CN (5 ml) under cold conditions (0-5° C.) and under argon. The reaction being complete from the end of the addition of the bromine, the reaction mixture is poured onto ice-cold water (600 ml). The aqueous phase is subsequently extracted with DCM (3×200 ml). The organic phases are combined, then washed with water and evaporated to dryness. The crude product obtained (3.5 g) is dissolved in the minimum amount of methanol and then brought to reflux in 10 ml of a 2N hydrochloric acid solution for 10 minutes. After cooling, the reaction mixture is washed with ether and then evaporated to dryness to give 1.4 g of the deprotected product 14 with a yield of 26% over the two stages.

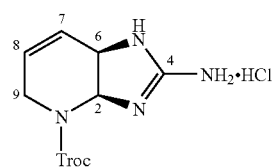

14

$^1$H NMR (250 MHz, d$_6$-DMSO): δ=3.74 (broad d, J=17 Hz, 1H, 9-H$_a$), 4.18 (broad d, J=17 Hz, H, 9-H$_b$), 4.50 (broad d, J=8 Hz, 1H, 6-H), 4.95 (m, 2H, H-Troc), 5.74 (d, J=9 Hz, 1H, 7-H), 6.07 (m, 1H, 8-H), 6.24 (d, J2-6=8 Hz, 1H, 2-H); $^{13}$C NMR (62.5 MHz, CD$_3$OD): δ=40.1 (C-9), 51.8 (C-6), 66.3 (C-2), 76.6 (CH$_2$-Troc), 122.9 (C-8), 127.0 (C-7), 156.0 (C-4), 160.0 (carbamate); MS(ES): m/z 313.0, 315.0, 317.0 [M]$^+$.

EXAMPLE 9

N-(1H-pyrrol-2-yl)guanidine formate 15

A solution of the mixture of isomers 2 and 3 (131 mg, 0.44 mmol) in 1M NaOH (10 ml) is heated at reflux for 20 min. After cooling to ambient temperature and neutralizing using a 1M HCl solution, the reaction mixture is concentrated to dryness. The solid residue is triturated with methanol and is then filtered. The filtrate is concentrated to dryness (333 mg) and then chromatographed on silica gel (acetone/AcOEt/H$_2$O/HCO$_2$H, 360:600:12:12 and then 300:500:50:50) to give 54 mg of 15 (R$_f$=0.44, acetone/AcOEt/H$_2$O/HCO$_2$H, 30:50:5:5) with a yield of 67%.

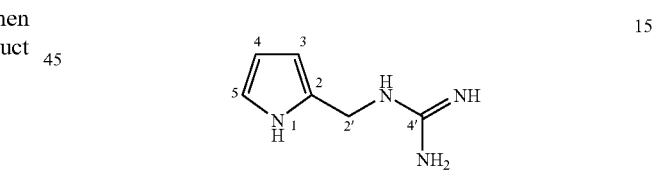

$^1$H NMR (300 MHz, CD$_3$OD): δ=3.34 (s, 2H, 2'-H), 6.04 (m, 1H, 3-H), 6.09 (m, 1H, 4-H), 6.73 (app s, 1H, 5-H), 8.58 (broad s, 1H, HCO$_2$D); $^{13}$C NMR (75.5 MHz, CD$_3$OD): δ=39.6 (C-2'), 108.4, 108.9 (C-3, C-4), 119.5 (C-5), 126.6 (C-2), 158.4 (C-4'); MS(ES): m/z 139.2 [M+H]$^+$; HRMS, calculated C$_6$H$_{10}$N$_4$ [M+H]$^+$: 139.09837. found: 139.09843.

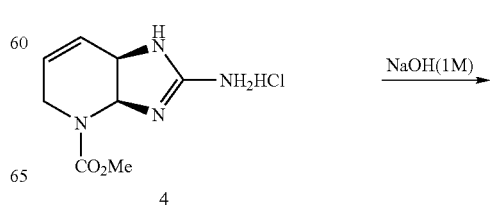

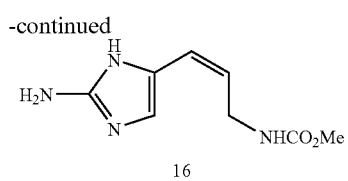

16

EXAMPLE 10

[3-(2-Amino-2,3-dihydro-1H-imidazol-4-yl)allyl]carbamic acid methyl ester 16

0.111 g (0.47 mmol) of the methyl ester of 2-amino-1,3a,5,7a-tetrahydroimidazo[4,5-b]pyridine-4-carboxylic acid 4 is added to 4 ml of a NaOH solution (1 ml). The reaction mixture is brought to reflux with stirring for 5 minutes (reaction monitored by TLC). After cooling, a phosphate buffer solution (pH=7) (20 ml) is added and the mixture is extracted with BuOH until exhausted. The organic phases are combined and evaporated to dryness to give 0.079 g of allyl amine 16 in the form of a brown solid with a yield of 85%.

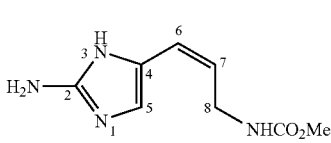

16

$^1$H NMR (300 MHz, $d_1$-TFA): δ=3.88 (s, 3H, OMe), 4.09 (dd, J=7 and 2 Hz, 2H, 8-H), 5.87 (dt, J=7 Hz, 12 Hz, 1H, 7-H), 6.23 (d, J=12 Hz, 1H, 6-H), 6.73 (s, 1H, 5-H); $^1$H NMR (300 MHz, CD$_3$OD): δ=3.64 (s, 3H, OMe), 3.96 (dd, J=7 and 1 Hz, 2H, 8-H), 5.37 (dt, J=7 and 11 Hz, 1H, 7-H), 6.15 (d, J=11 Hz, 1H, 6-H), 6.51 (s, 1H, 5-H); $^{13}$C NMR (75.5 MHz, CD$_3$OD): δ=41.0 (C-8), 52.5 (OMe), 118.0 (C-5), 121.0 (C-6), 125.0 (C-7), 130.0 (C-4), 151.0, 160.0 (C-2 and CO carbamate); MS(ES): m/z 197.1 [M+H]$^+$; HRMS, calculated C$_8$H$_{12}$O$_2$N$_4$ [M+H]$^+$: 197.10385, found: 197.10395.

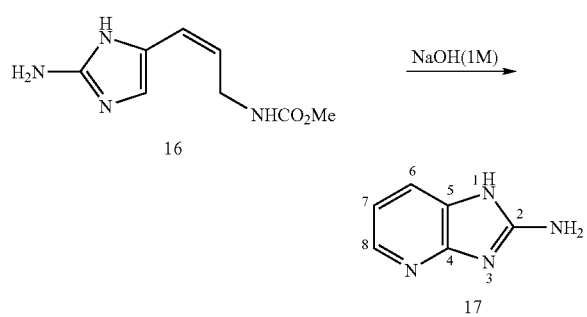

EXAMPLE 11

1H-Imidazo[4,5-b]pyridin-2-ylamine 17

20 mg (0.1 mmol) of the cis allyl amine 16 are dissolved in a 1M NaOH solution (2 ml). The mixture is left at ambient temperature for 48 h. This solution is extracted with BuOH (3×20 ml). The butanol phases are combined and evaporated to dryness. The residue is taken up in the minimum amount of methanol and then purified on preparative silica gel plates using the DCM/MeOH(NH$_3$), 8/2, mixture as eluent. Compound 17 (4 mg) is obtained with a yield of 31%.

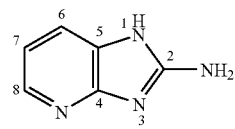

17

$^1$H NMR (300 MHz, CD$_3$OD): =6.69 (dd, J=7 and 7 Hz, 1H, H-7), 7.41 (d, J=7 Hz, 1H, H-6), 7.88 (d, J=6.5 Hz, 1H, H-8); $^{13}$C NMR (75.5 MHz, CD$_3$OD): δ=117.3 (C-7), 119.4 (C-6), 141.0 (C-8), MS(ES): m/z 135.2 [M+H]$^+$.

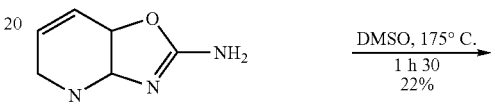

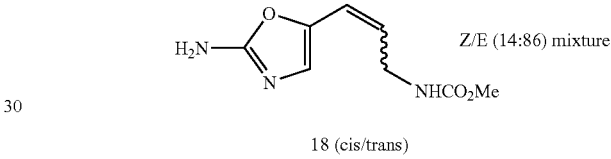

18 (cis/trans)

EXAMPLE 12

[3-(2-Aminooxazol-5-yl)allyl]carbamic acid methyl ester 18

A solution of product 5 (1.2 g, 6.1 mmol, 0.08M) in DMSO (75.5 ml) is heated at 175° C. for 1 h 30. After cooling at ambient temperature, the reaction mixture is poured onto water (200 ml), basified (5% Na$_2$CO$_3$) to a pH of greater than 10 and then extracted with DCM (4×150 ml). The aqueous phase is then saturated with NaCl and then extracted with DCM (4×150 ml). The organic phases are combined, dried (MgSO$_4$) and then evaporated. The crude product obtained (6.6 g) is then purified by chromatography on silica gel (DCM (sat. NH$_3$) and then DCM (sat. NH$_3$)/MeOH, 98/2). Product 18 (R$_f$=0.36, DCM/MeOH(NH$_3$): 98/2) is obtained in the form of a brown semisolid (265 mg, 22%), an inseparable mixture of Z/E (14:86) isomers.

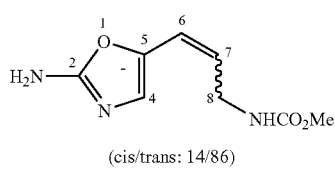

18

(cis/trans: 14/86)

(E)-18: $^1$H NMR (300 MHz, CD$_3$OD): δ=3.64 (s, 3H, OMe), 3.80 (d, J=7 Hz, 2H, 8-H), 5.85 (dt, J=6 and 16 Hz, 1H, 7-H), 6.22 (dd, J=16 and 1 Hz, 1H, 6-H), 6.54 (s, 1H, 4-H); $^{13}$C NMR (75.5 MHz, CD$_3$OD): δ=43.3 (C-8), 52.6 (OMe), 117.4 (C-6), 123.8 (C-7), 124.4 (C-4), 144.7 (CO carbamate), 159.5, 163.1 (C-2, C-5). (Z)-18: $^1$H NMR (300 MHz, CD$_3$OD): δ=3.64 (s, 3H, 12-H), 4.06 (broad d, J=6 Hz, 1H, 8-H), 5.36 (dt, J=6 and 12 Hz, 1H, 7-H), 6.09 (dd, J=12 and 1 Hz, 1H, 6-H), 6.63 (s, 1H, 4-H). $^{13}$C NMR (75.5 MHz, CD$_3$OD): δ=40.9 (C-8), 52.5 (OMe), 115.8 (C-6), 125.6 (C-7), 126.7 (C-4), 144.5 (CO carbamate) (C-2, C-5, undetected). MS(ES): m/z 197.8 [M+H]$^+$.

EXAMPLE 12A

[3-(2-Imino-2,3-dihydrothiazol-5-yl)allyl]carbamic acid methyl ester

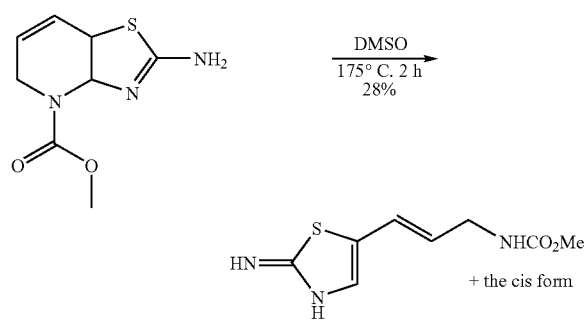

Compound 6 (0.070 g, 0.32 mmol) is heated in DMSO (5 ml) at 175° C. for 2 h. After cooling to ambient temperature, the reaction mixture is poured onto ice-cold water (100 ml), basified (5% Na$_2$CO$_3$) to a pH of greater than 10 and then extracted with DCM (3×150 ml). The organic phases are combined, washed with saturated NaCl solution, dried (MgSO$_4$) and then evaporated to dryness. The crude product obtained (0.06 g) is then purified by chromatography on thick layers of silica gel (DCM, sat. NH$_3$/MeOH, 95:5). The product (R$_f$=0.49, DCM/MeOH/NH$_3$ vap., 95:5) is obtained in the form of a brown semisolid (20 mg, 0.09 mmol, 28%), an inseparable mixture of E/Z (9:1) isomers according to $^1$H NMR.

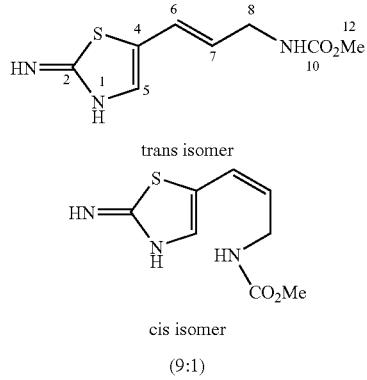

[3-(2-Imino-2,3-dihydrothiazol-5-yl)allyl]carbamic acid methyl ester (E isomer): $^1$H NMR (300 MHz, CDCl$_3$): δ=3.64 (s, 3H, H-12), 3.8 (d, J=5 Hz, 2H, H-8), 5.57 (dt, J=6 and 15 Hz, 1H, H-7), 6.45 (d, LJ=15 Hz, 1H, H-6), 6.85 (s, 1H, H-5); $^{13}$C NMR (75.5 MHz, CDCl$_3$): δ=42.4 (C-8), 51.9 (C-12), 122.0 (C-6), 124.1 (C-7), 125.8 (C-4), 136.4 (C-5), 157.4 (C-10), 168.1 (C-2). MS(ES): m/z=214[M+H]$^+$; MS(HR) (ES): calculated C$_8$H$_{11}$N$_3$O$_2$S, found 214.0650. [M+H]$^+$, IR, (CHCl$_3$, cm$^{-1}$): 1699, 1636, 1536, 1503, 1023, 949.

(Z isomer): $^1$H NMR (300 MHz, CDCl$_3$): δ=3.64 (S, 3H, H-12), 3.77 (d, J=5 Hz, 2H, H-8), 5.36 (dt, J=6 and 11 Hz, 1H, H-7), 6.37 (d, J=11 Hz, 1H, H-6), 6.93 (s, 1H, H-5).

(Z isomer not isolated, values taken from the actual spectrum of the E isomer).

EXAMPLE 13

(cis)-2-Oxo-1,2,3,3a,5,7a-hexahydro-imidazo[4,5-b]pyridine-4-carboxylic acid methyl ester 19

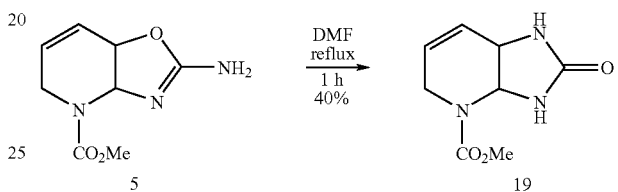

A solution of 5 (200 mg, 1 mmol) in DMF (10 ml) is brought to reflux for 1 h. After evaporating the solvent, the crude product (280 mg) is purified by chromatography on silica gel (Et$_2$O/MeOH, 93:7). Product 19 (R$_f$=0.36, Et$_2$O/MeOH, 92:8) is obtained in the form of a yellow solid (81 mg, 40%).

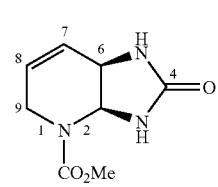

$^1$H NMR (250 MHz, d$_6$-DMSO): δ=3.55 (broad d, 1H, 9-H$_a$), 3.65 (s, 3H, OCH$_3$), 4.06 (m, 2H, 9-H$_b$, 6-H), 5.56 (m, 1H, 7-H), 5.86 (m, 2H, 8-H, 2-H), 6.52 (broad s, NH), 6.76 (broad s, NH). $^1$H NMR (250 MHz, CD$_3$OD): δ=3.67 (broad d, 1H, 9-H$_a$), 3.76 (s, 3H, OCH$_3$), 4.17 (m, 2H, 9-H$_b$, 6-H), 5.66 (m, 1H, 7-H), 5.95 (m, 1H, 8-H), 6.14 (broad d, J=8 Hz, 1H, 2-H). $^{13}$C NMR (75.5 MHz, d$_6$-DMSO): δ=38.2 (C9), 48.0 (C6), 52.7 (OCH$_3$), 61.7 (C2), 123.9 (C8), 124.3 (C7), 155.3 (CO carbamate), 160.98 (C4). MS(ES): m/z 219.9 [M+Na]$^+$.

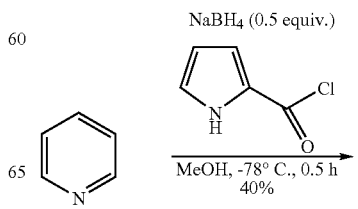

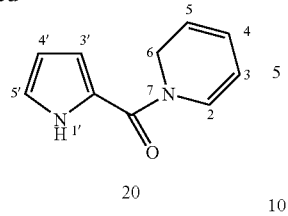

20

EXAMPLE 14

(2H-Pyridin-1-yl)(1H-pyrrol-2-yl)methanone 20

Pyrrolic acid (1.11 g, 10.0 mmol, 1 equiv.) is suspended in toluene (20 ml) under argon. Oxalyl chloride (2 ml, 23.0 mmol, 2.3 equiv.) is rapidly added dropwise and then one drop of DMF is added, which brings about the evolution of gas and dissolution of the product. After leaving overnight at ambient temperature, the reaction medium is concentrated under reduced pressure and dried using pump vacuum for 2 h.

The acid chloride thus obtained is taken up in dichloromethane (10 ml) and introduced into a two-necked flask under argon. Pyridine (0.8 ml, 10.0 mmol, 1 equiv.) is added to this solution. After 1 h at ambient temperature, the precipitate formed is dried. It is taken up in methanol (10 ml) and cooled to −78° C., and NaBH$_4$ (0.19 g, 5.0 mmol, 0.5 equiv.) is added. The reaction medium is stirred at the same temperature for 30 min, and then it is poured onto ice-cold water (50 ml) and extracted with diethyl ether (2×50 ml). The organic phase is dried over magnesium sulfate and then concentrated under reduced pressure. The residue is purified by chromatography on a column of alumina gel eluted with dichloromethane. The dihydropyridine 20 is obtained with a yield of 39% (0.68 g).

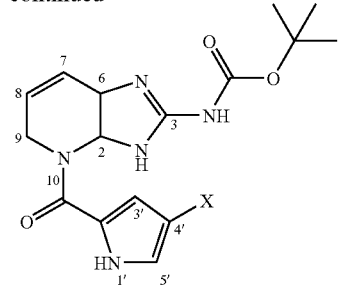

20

$^1$H NMR (300 MHz, CDCl$_3$): δ=9.70 (bs, 1H), 7.08 (d, J=7.6 Hz, 1H, H2), 6.99 (m, 1H, H5'), 6.67 (m, 1H, H3'), 6.30 (m, 1H, H4'), 5.98 (m, 1H, H4), 5.70 (m, 1H, H5), 5.38 (dd, J=7.6 and 7.6 Hz, 1H, H3); $^{13}$C NMR (75.5 MHz): 149.9 (C7), 127.5 (C2), 124.3 (C2'), 122.6 (C5'), 122.4 (C3), 120.4 (C5), 114.6 (C4), 110.1 (C4'), 107.3 (C5), 44.8 (C6); MS(ESI+): 175.1 [M+H$^+$]; 197.0 [M+Na]; 215.0 [M+K].

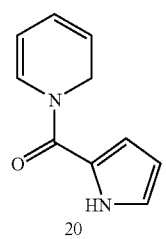

| | Boc-guanidine (4 equiv.) Br$_2$ (1 equiv.) |
|---|---|
| | DMF/CH$_3$CN (4:1) AT, 15 min, 28% |

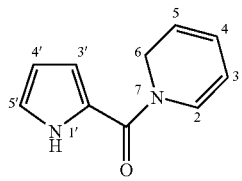

21:X = H

EXAMPLE 15

[4-(1H-Pyrrolyl-2-carbonyl)-3a,4,5,7a-tetrahydro-3H-imidazo[4,5-b]pyridin-2-yl]carbamic acid tert-butyl ester 21

The dihydropyridine 20 (0.50 g, 2.8 mmol, 1 equiv.) and N-Boc-guanidine (1.36 g, 8.4 mmol, 3 equiv.) are suspended in a mixture of DMF/CH$_3$CN 3/1 (8 ml). Bromine (0.14 ml, 2.8 mmol, 1 equiv.), in solution in DMF (2 ml), is added dropwise to this suspension over a period of 15 min. From the end of the addition, the reaction mixture is concentrated under reduced pressure and then dried using pump vacuum. The residue is purified by chromatography on a column of silica gel eluted with a CH$_2$Cl$_2$ saturated with ammonia/MeOH 99/1 mixture. The coupling product 21 is obtained with a yield of 28% (0.26 g).

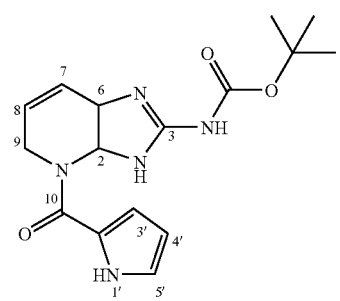

21

$^1$H NMR (300 MHz, CD$_3$OD): 6.97 (m, 1H, H5'), 6.90 (d, J=8.0 Hz, 1H, H2), 6.68 (m, 1H, H3'), 6.24 (dd, J=2.4 and 3.5 Hz, 1H, H4'), 5.86 (dd, J=4.0 and 10 Hz, 1H, H8), 5.70 (bd, J=10.0 Hz, 1H, H7), 4.66 (m, 1H, H9), 4.59 (m, 1H, H6), 4.25 (m, 1H, H9); MS(ES): 354.15 [M+Na$^+$]; 197.0 [M+Na$^+$]; 332.15 [M+H$^+$]; 232.08 [M−Boc]$^+$.

EXAMPLE 16

[4-(4-Bromo-1H-pyrrolyl-2-carbonyl)-3a,4,5,7a-tetrahydro-3H-imadazo[4,5-b]pyridin-2-yl]carbamic acid tert-butyl ester 22

Same procedure as for 21 but with 2 equiv. of Br$_2$ (optimized yield of 19%).

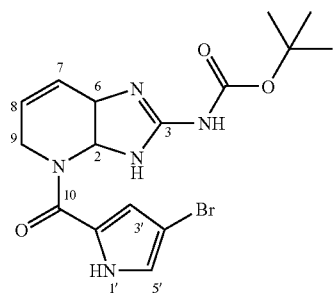

22

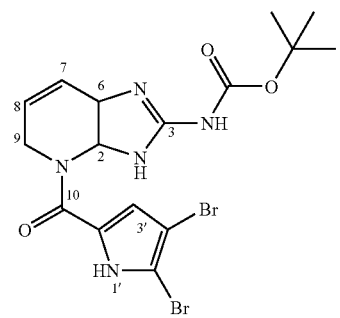

23

¹H NMR (300 MHz, CD₃OD): 7.00 (d, J=1.0 Hz, 1H, H5') 6.84 (d, J=8.5 Hz, 1H, H2), 6.72 (m, 1H, H3'), 5.85 (dd, J=4.8, 9.6 Hz, 1H, H7), 5.72 (bd, J=10.3 Hz, 1H, H8), 4.60 (dd, J=4.7, 17.5 Hz, 1H, H6), 4.27 and 4.03 (2m, 2H, H9); ¹³C NMR (75.5 MHz): 28.1 ((CH₃)₃), 40.0 (C9), 52.6 (C6), 79.4 (CtBu), 8.6 (C2), 97.5 (C4'), 115.6 (C8), 123.6 (C3'), 124.8 (C7), 126.5 (C7), 127.7 (C5'), 146.3 and 167.0 (C10 and CO carbamate); MS(ES): 412.1-410.1 [M+H⁺], 332.2 [M–HBr]⁺, 312.0-310.0 [M–Boc]⁺, 232.1 [M–2HBr]⁺.

¹H NMR (300 MHz, CD₃OD): 6.84 (s, 1H, H3'), 6.67 (d, J=8.5 Hz, 1H, H2), 6.17 (td, J=2.5 and 10.5 Hz, 1H, H8), 5.80 (dd, J=1.6 and 10.5 Hz, 1H, H7), 4.62 (d, 1H, H6), 4.53 and 4.03 (2m, 2H, H9); ¹³C NMR (75.5 MHz): 27.8 ((CH₃)₃), 41.7 (C9), 53.1 (C6), 76.1 (CtBu), 84.7 (C2), 95.8 (C4'), 97.2 (C3'), 103.8 (C5'), 114.9 (C8), 124.4 (C2'), 126.5 (C7), 152.2 and 161.8 (C10 and CO carbamate); MS(ES): 490.0 [M+H⁺], 410.1 [M–HBr]⁺, 389.9 [M–Boc]⁺, 332.1 [M–2HBr]⁺, 310.0 [M–HBr–Boc]⁺, 232.1 [M–2HBr–Boc]⁺

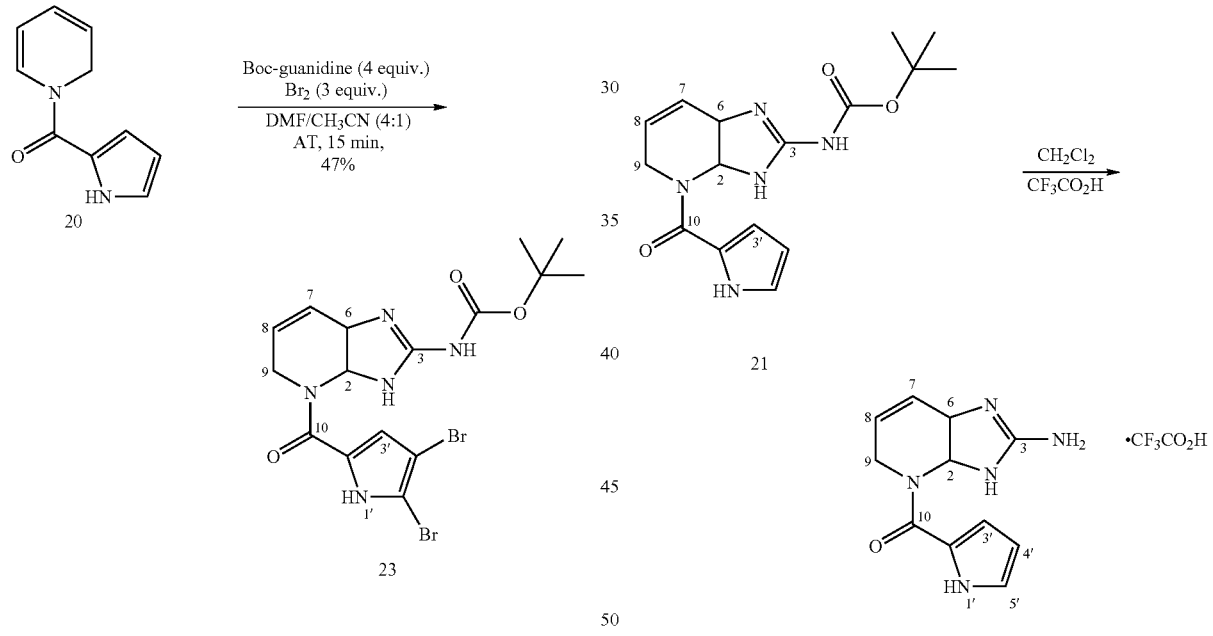

EXAMPLE 17

[4-(4,5-Dibromo-1H-pyrrolyl-2-carbonyl)-3a,4,5,7a-tetrahydro-3H-imidazo[4,5-b]pyridin-2-yl]carbamic acid tert-butyl ester 23

Compound 20 (0.24 g, 1.4 mmol, 1 equiv.) and N-Boc-guanidine (0.65 g, 4.1 mmol, 4 equiv.) are suspended in a DMF/CH₃CN 3/1 mixture (8 ml). Bromine (0.21 ml, 4.2 mmol, 3 equiv.), in solution in DMF (2 ml), is added dropwise over a period of 15 min. From the end of the addition, the reaction mixture is concentrated under reduced pressure and dried using pump vacuum. The residue is purified by chromatography on a column of silica gel eluted with a CH₂Cl₂ saturated with ammonia/MeOH 99/1 mixture. The product 23 is obtained with a yield of 47% (0.31 g).

EXAMPLE 18

[4-(1H-Pyrrolyl-2-carbonyl)-3a,4,5,7a-tetrahydro-3H-imidazo[4,5-b]pyridin-2-yl]carbamic acid 24

Compound 21 (0.15 g, 0.3 mmol, 1 equiv.) is dissolved in dichloromethane (3 ml) and then the same volume of trifluoroacetic acid is added. The reaction mixture is stirred at ambient temperature until the starting material has been completely consumed. The mixture is then concentrated under reduced pressure and dried using pump vacuum for 2 h. The residue is purified by chromatography on a column of silica gel eluted with a CH$_2$Cl$_2$ saturated with ammonia/MeOH 9/1 mixture. The product 24 is obtained with a yield of 68% (0.11 g).

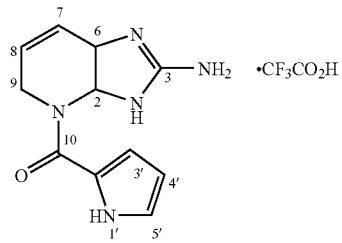

$^1$H NMR (300 MHz, CD$_3$OD) 6.99 (m, 1H, H5'), 6.81 (d, J=8.3 Hz, 1H, H2), 6.73 (dd, J=1.2 and 3.6 Hz, 1H, H3'), 6.24 (dd, J=2.4, 3.6 Hz, 1H, H4'), 6.5 (ddd, J=1.9, 5.0 and 10.3 Hz, 1H, H8), 5.76 (dd, J=1.8 and 10.3 Hz, 1H, H7), 4.67 (dd, J=5.0 and 18.0 Hz, 1H, H9), 4.52 (d, J=8.4 Hz, 1H, H6), 3.95 (d, J=18.0 Hz, 1H, H9); $^{13}$C NMR (75.5 MHz): 39.4 (C9), 50.1 (C6), 64.9 (C2), 108.7 (C4'), 113.3 (C3'), 121.5 (C8), 122.2 (C5'), 122.7 (C2'), 126.5 (C7), 158.7 (C10), 163.5 (C4).

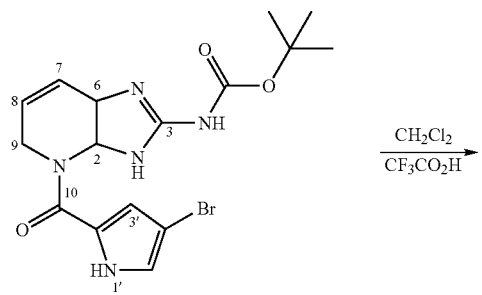

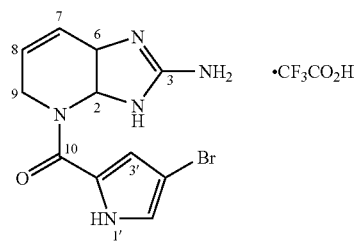

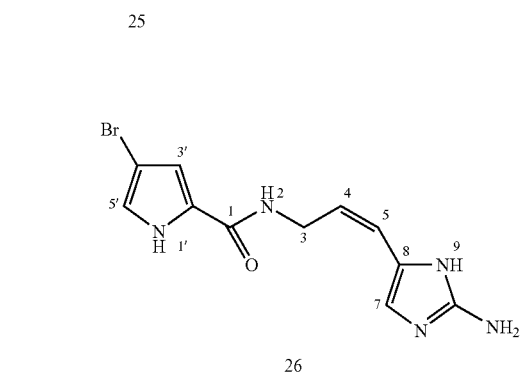

EXAMPLE 19

[4-(1H-Pyrrolyl-2-carbonyl)-3a,4,5,7a-tetrahydro-3H-imidazo[4,5-b]pyridin-2-yl]carbamic acid 25 and Its Product of Opening 26

The bicycle 22 (50 mg, 0.12 mmol, 1 equiv.) is dissolved in dichloromethane (1 ml). An equivalent volume of trifluoroacetic acid is added to it and the medium is stirred at ambient temperature until the starting material has been completely consumed. The reaction mixture is then concentrated under reduced pressure and dried using pump vacuum for 2 h. The residue is purified by preparative thin layer chromatography, eluted with a CH$_2$Cl$_2$ saturated with ammonia/MeOH 9/1 mixture. The products 25 and 26 (cis-hymenidin) are obtained with yields of 52% and 15% respectively.

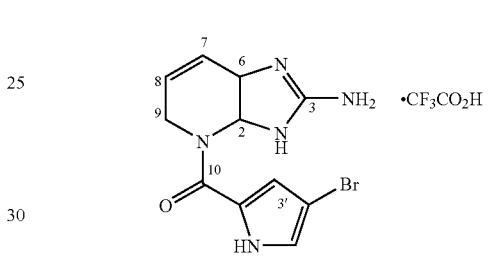

$^1$H NMR (300 MHz, CD$_3$OD): 7.02 (d, J=1.2 Hz, 1H, H5'), 6.76 (d, J=1.2 Hz, 1H, H3'), 6.73 (d, J=1.2 Hz, 1H, H2), 6.15 (ddd, J=1.7, 4.8 and 10.3 Hz, 1H, H8), 5.77 (dd, J=2.0 and 10.3 Hz, 1H, H7), 4.65 (dd, J=4.8, 17.8 Hz, 1H, H9), 4.53 (d, J=8.2 Hz, 1H, H6), 3.96 (d, J=18.0 Hz, 1H, H9); $^{13}$C NMR (75.5 MHz): 40.9 (C9), 51.8 (C6), 66.5 (C2), 97.6 (C4'), 116.2 (C3'), 123.1 (C8), 123.8 (C5'), 125.1 (C2'), 128.0 (C7), 160.3 (C10), 163.1 (C4); MS(ES): 312.0-310.0 [M+H$^+$], 232.1 [M−HBr]$^+$.

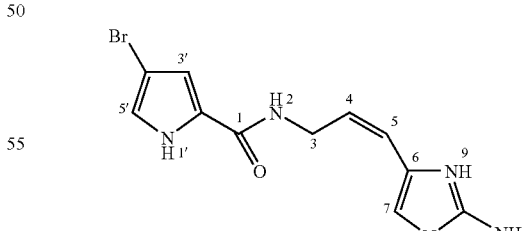

$^1$H NMR (300 MHz, CD$_3$OD): 6.90 (d, J=1.4 Hz, 1H, H5') 6.77 (d, J=1.4 Hz, 1H, H3'), 6.59 (s, 1H, H6), 6.20 (d, J=11.6 Hz, 1H, H5), 5.48 (dt, J=6.7 and 11.6 Hz, 1H, H4), 4.16 (dd, J 1.3 and 6.7 Hz, 2H, H3);

$^{13}$C NMR (75.5 MHz): 39.5 (C3), 97.65 (C4'), 113.5 (C3'), 118.1 (C7), 121.4 (C5), 123.0 (C4), 125.5 (C5'), 125.9 (C2').

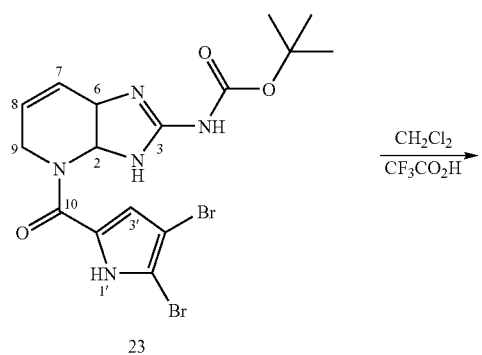
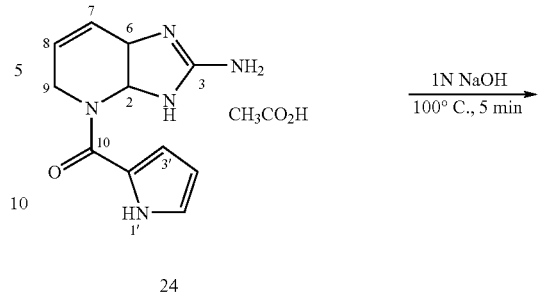

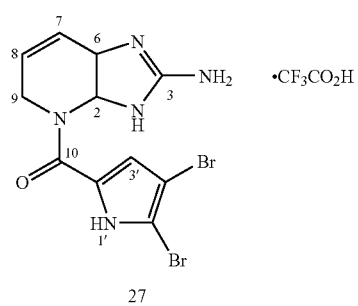

EXAMPLE 19

[4-(4,5-Dibromo-1H-pyrrolyl-2-carbonyl)-3a,4,5,7a-tetrahydro-3H-imidazo[4,5-b]pyridin-2-yl]carbamic acid 27

Compound 23 (30 mg, 0.06 mmol, 1 equiv.) is dissolved in dichloromethane (2 ml). An equivalent volume of trifluoroacetic acid is added and the medium is stirred at ambient temperature until the starting material has been completely consumed. The mixture is then concentrated under reduced pressure and dried using pump vacuum for 2 h. The residue is purified with preparative plates eluted with a $CH_2Cl_2$ saturated with ammonia/MeOH 9/1 mixture. The deprotected product 27 is obtained with a yield of 53% (16 mg).

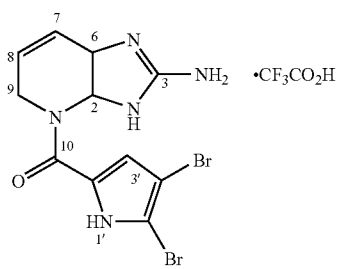

27

$^1$H NMR (300 MHz, $CD_3OD$): 6.80 (s, 1H, H3'), 6.70 (d, J=8.6 Hz, 1H, H2), 6.15 (ddd, J=2.2, 5.0 and 10.3 Hz, 1H, H8), 5.76 (dd, J=1.8 and 10.3 Hz, 1H, H7), 4.62 (dd, J=1.8, 10.3 Hz, 1H, H9), 4.54 (dd, J=2.7 Hz, 1H, H6), 3.98 (d, J=16.0 Hz, 1H, H9); MS(ESI+): 392.0-390.0-388.0 [M+H$^+$]; 312.0-310.0 [M-HBr]$^+$; 232.1 [M-2HBr]$^+$.

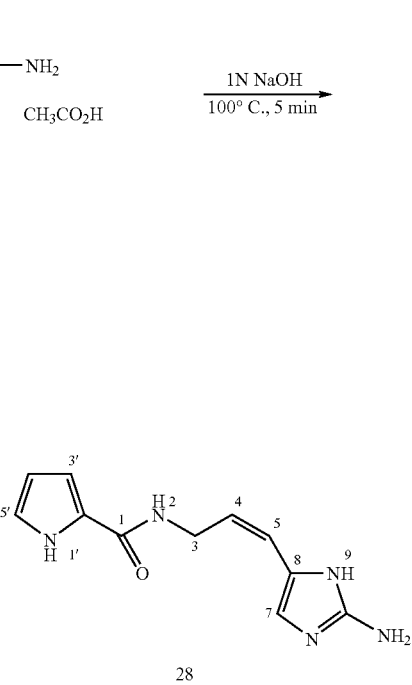

EXAMPLE 20

Cis-clathrodin 28

The bicycle 24 (100 mg, 0.3 mmol, 1 equiv.) is suspended in a 1N sodium hydroxide solution (2 ml) and heated at 100° C. for 5 min. After returning to ambient temperature, the reaction medium is extracted with ethyl acetate (4×5 ml). The organic phase is dried over magnesium sulfate and concentrated under reduced pressure. Clathrodin 28 is obtained with a nonoptimized yield of 25% (17 mg).

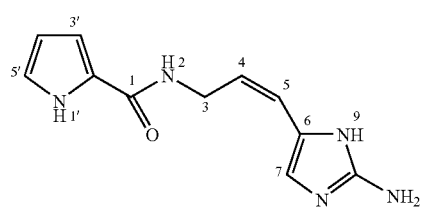

28

$^1$H NMR (300 MHz, $CD_3OD$): 6.90 (m, 1H, 5'H), 6.76 (dd, 1H J=1.4, 3.7 Hz, 1H, H3'), 6.65 (s, 1H, H6), 6.21 (dd, J=11.7 Hz, 1H, H5), 6.15 (m, 1H, H4'), 5.56 (dt, J=6.8, 11.7 Hz, 1H, H4), 4.14 (dd, J=1.7 and 6.8 Hz, 2H, H3); $^{13}$C NMR (75.5 MHz): 163.8 (C8), 151.3 (C1), 129.9 (C6), 126.8 (C2'), 125.0 (C5'), 122.9 (C4), 121.3 (C5), 118.6 (C7), 111.8 (C3'), 110.2 (C4'), 39.3 (C3).

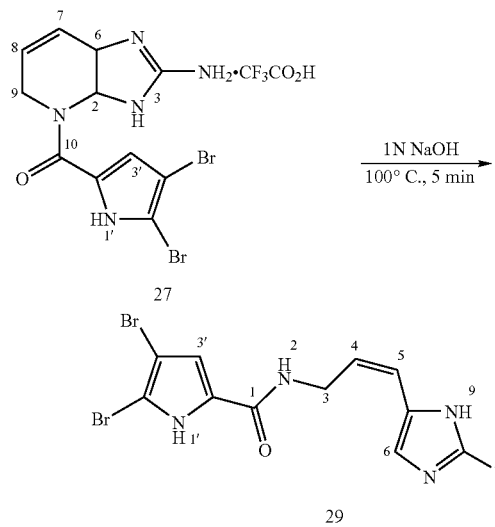

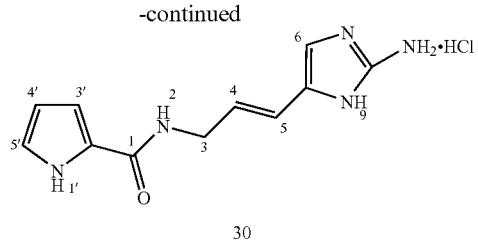

EXAMPLE 22

Clathrodin 30 cis-ClathrodinAcOH 28 (24 mg, 0.08 mmol, 1 equiv.) is dissolved in methanol (0.5 ml) and then a 6N HCl solution (0.6 ml) is added. The reaction medium is heated at 60° C. for 24 h. After returning to ambient temperature and concentrating the mixture to dryness under reduced pressure, the residue is treated with preparative plates eluted with a $CH_2Cl_2$ saturated with ammonia/MeOH 9/1 mixture. The product 30 is obtained with a yield of 24% (5 mg). The physical characteristics are identical to those in the literature.

EXAMPLE 21

Synthesis of Cis-oroidin 29

The bicycle 27 (16 mg, 0.03 mmol, 1 equiv.) is suspended in a 1N sodium hydroxide solution (1 ml) and heated at 100° C. for 10 min. After returning to ambient temperature, the medium is extracted with ethyl acetate (5×5 ml). The organic phase is dried with magnesium sulfate and concentrated under reduced pressure, the residue is redissolved in a few drops of methanol and one drop of acetic acid, and then drying is carried out. The salt of the product 29 is obtained with a yield of 85% (13 mg).

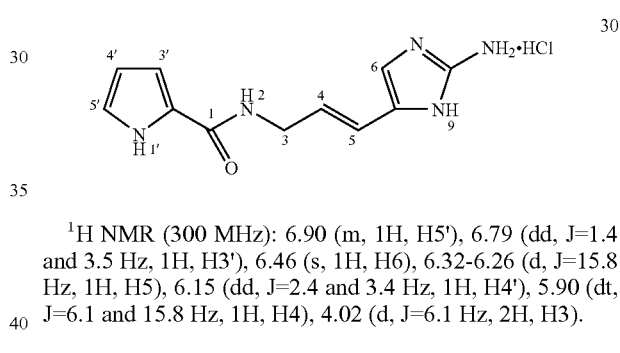

$^1$H NMR (300 MHz): 6.90 (m, 1H, H5'), 6.79 (dd, J=1.4 and 3.5 Hz, 1H, H3'), 6.46 (s, 1H, H6), 6.32-6.26 (d, J=15.8 Hz, 1H, H5), 6.15 (dd, J=2.4 and 3.4 Hz, 1H, H4'), 5.90 (dt, J=6.1 and 15.8 Hz, 1H, H4), 4.02 (d, J=6.1 Hz, 2H, H3).

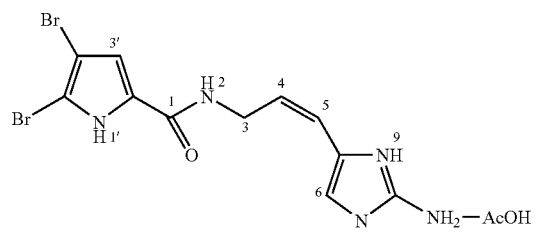

$^1$H NMR (300 MHz, $CD_3OD$): 6.82 (s, 1H, H3'), 6.79 (s, 1H, H6), 6.20 (d, J=11.5 Hz, 1H, H5), 5.74 (td, J=7.1 and 11.5 Hz, 1H, H4), 4.08 (d, J=7.1 Hz, 2H, H3), 1.96 (s, 3H, ACOH); MS(ES): 391.96-389.97-387.97 $(M+H)^+$; 310.04 $(M-HBr)^+$; 232.10 $(M-2HBr)^+$.

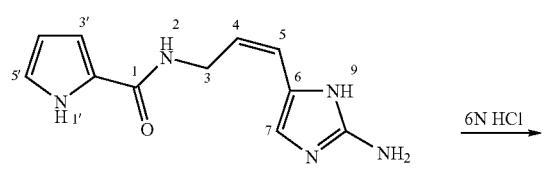

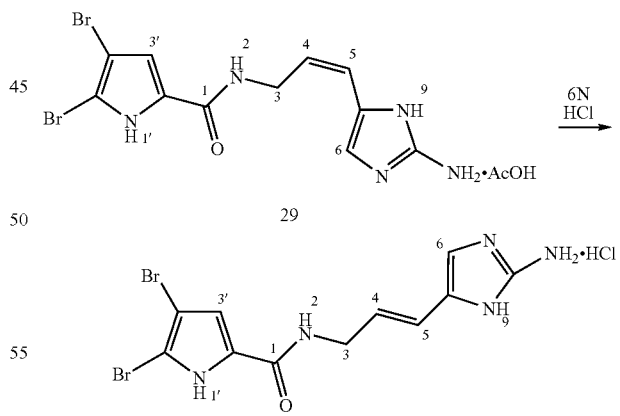

EXAMPLE 23

Synthesis of Oroidin 31 cis-Oroidin.AcOH 29 (12 mg, 0.03 mmol, 1 equiv.) is dissolved in methanol (0.4 ml), then 0.6 ml of a 6N HCl solution is added and the medium is heated at 60° C. for 24 h. After returning to ambient temperature, the medium is concentrated under reduced pressure and dried using pump vacuum. The residue is purified with preparative plates eluted with a CH$_2$Cl$_2$ saturated with ammonia/MeOH 9/1 mixture. Oroidin 31 is obtained with a yield of 44% (5 mg). The physical characteristics are identical to those in the literature.

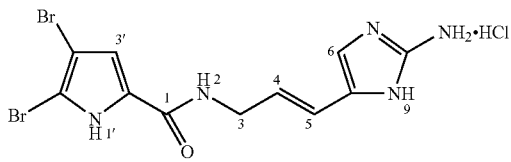

$^1$H NMR (300 MHz, CD$_3$OD): 6.82 (s, 1H, H3'), 6.49 (s, 1H, H6), 6.31-6.26 (d, J=15.7 Hz, 1H, H5), 5.92 (td, J=6.0, 15.7 Hz, 1H, H4), 4.0 (d, J=6.0 Hz, 2H, H3).

EXAMPLE 24

2-Imino-2,3,5,6-tetrahydro-1H-1,3,5-triazaazulen-4-one

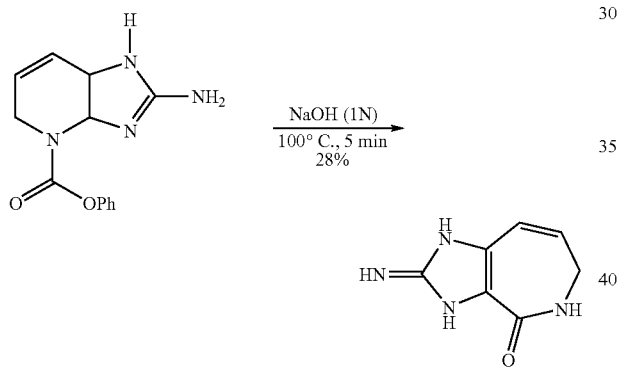

Compound 10 (0.134 g, 0.4 mmol), 2-amino-1,3a,5,7a-tetrahydroimidazo[4,5-b]pyridine-4-carboxylic acid methyl ester hydrochloride, is added to 4 ml of a 1M NaOH solution. The reaction mixture is brought to reflux with stirring for 5 minutes (reaction monitored by TLC). After cooling, water (20 ml) is added and the mixture is extracted with BuOH until exhausted. The organic phases are combined and evaporated to dryness to give 0.467 g of a crude product which, after separation with silica plates using the ACUE/acetone/HCO$_2$H/H$_2$O 5/3/0.5/0.5 mixture, gives 40 mg of 32 (0.24 mmol), i.e. a yield of 28%.

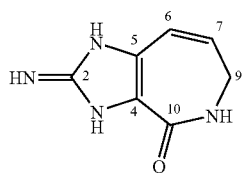

2-Imino-2,3,5,6-tetrahydro-1H-1,3,5-triazaazulen-4-one $^1$H NMR (300 MHz, CD$_3$OD): δ=3.48 (d, J=6 Hz, 2H, H-8), 5.88 (dt, J=6 and 11 Hz, 1H, 7-H), 6.52 (d, J=11 Hz, 1H, 6-H). $^{13}$C NMR (75.5 MHz, CD$_3$OD): δ 38.4 (C-8), 124.6 (C-7), 126.5 (C-6), 159.7 (C-2), 162.9 (C-10). MS(ES): m/z=165 [M+H]$^+$, 187.0526 [M+Na]$^+$; HRMS(ES): calculated for C$_7$H$_8$N$_4$O: 165.0776; found 165.0785; IR (cm$^{-1}$) CHCl$_3$: 2928, 1669, 1630, 1645, 1079, 786.

What is claimed is:

1. A process for the synthesis of a heterocyclic compound, wherein the process comprises the opening of a compound of formula I:

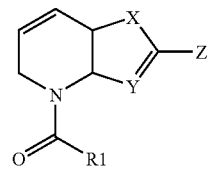

(I)

in which,
X represents NH, or an N-p group, p being a protective group,
Y represents N, O or S,
Z represents NH$_2$ or NH-p, and
R$_1$ represents a C$_1$-C$_6$ alkoxy radical, an aryloxy radical, optionally being substituted, or a salt or isomer of the compound,
said stage of opening being carried out under conditions resulting in a heterocycle of formula II:

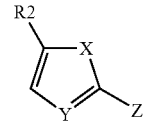

(II)

in which,
X, Y and Z are as defined above, and
R$_2$ represents a free allylamine chain or an allylamine chain protected in the carbamate form, —CH=CH—CH$_2$—NH$_2$R$_1$, allylamide —CH=CH—CH$_2$—NH—COR$_1$ or

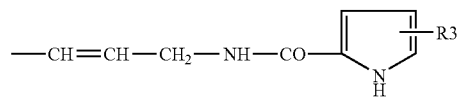

group,
R$_3$ occupying one, two or three positions and representing a halogen.

2. The process as claimed in claim 1, wherein the stage of opening the bicycle is carried out in an alkaline medium or in a solvent by heating at reflux.

3. The process as claimed in claim 1, wherein, when R$_1$ represents a pyrrolyl group, optionally substituted, the bicycle is reacted, in solution in a solvent with trifluoroacetic acid at ambient temperature.

4. The process as claimed in claim 1, wherein the stage of opening is carried out on a mixture of regioisomers of formula I.

5. The process as claimed in claim 1, wherein use is made of a salt of a compound of formula I.

6. The process as claimed in claim 1, wherein the compound of formula I is a hydroimidazopyridine.

7. The process as claimed in claim 6, wherein the compound is a hydroimidazopyridine of formula III:

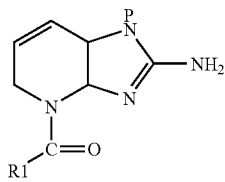
(III)

or of formula IV:

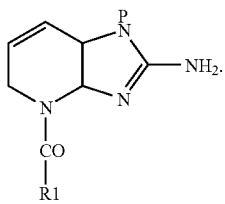
(IV)

8. The process as claimed in claim 7, wherein the stage of opening is carried out on a hydroimidazopyridine salt of formula V or VI:

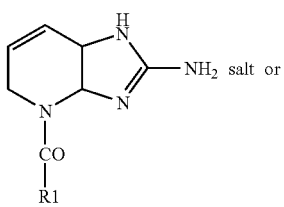
(V)

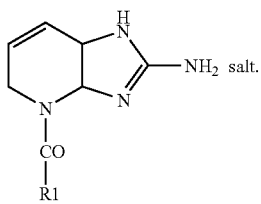
(VI)

9. The process as claimed in claim 1, wherein the compound of formula I subjected to the stage of opening is a hydrooxazopyridine.

10. The process as claimed in claim 9, wherein the hydrooxazopyridine corresponds to the formula VII:

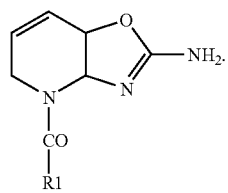
(VII)

11. The process as claimed in claim 10, wherein, on bringing to reflux a solution of said compound in a solvent a bicycle of formula VIII is obtained.

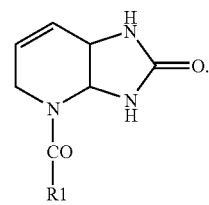
(VIII)

12. The process as claimed in claim 1, wherein the compound of formula I is a hydrothiazopyridine.

13. The process as claimed in claim 1, wherein the bicycle of formula I is obtained by reaction of a dihydropyridine of formula IX:

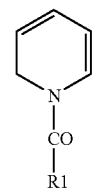
(IX)

with a derivative of formula X:

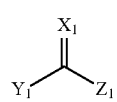
(X)

in which:
$X_1$ represents O, S or NH, and
$Y_1$ and $Z_1$ represent $NH_2$.

14. The process as claimed in claim 13, wherein the reaction between the compound of formulae IX and X is carried out in the presence of bromine in organic solvents at ambient temperature and under argon.

15. The process as claimed in claim 1 wherein the protecting group is Boc or Troc.

16. The process as claimed in claim 2 wherein the solvent is DMSO.

17. The process as claimed in claim 3 wherein the solvent is dichloromethane.

18. The process as claimed in claim 11 wherein the solvent is DMF.

19. The process as claimed in claim 14 wherein the organic solvents are DMF and/or $CH_3CN$.

20. The process as claimed in claim 1 wherein the aryloxy radical is a phenyloxy radical or a pyrrolyl radical.

* * * * *